(12) United States Patent
Michelson

(10) Patent No.: US 9,078,768 B2
(45) Date of Patent: *Jul. 14, 2015

(54) ARCUATE INTERBODY SPINAL FUSION IMPLANT HAVING A REDUCED WIDTH AND AN ANATOMICALLY CONFORMED TRAILING END

(75) Inventor: Gary K. Michelson, Venice, CA (US)

(73) Assignee: WARSAW ORTHOPEDIC, INC., Warsaw, IN (US)

(*) Notice: Subject to any disclaimer, the term of this patent is extended or adjusted under 35 U.S.C. 154(b) by 1462 days.

This patent is subject to a terminal disclaimer.

(21) Appl. No.: 11/133,528

(22) Filed: May 20, 2005

(65) Prior Publication Data

US 2005/0216089 A1 Sep. 29, 2005

Related U.S. Application Data

(60) Division of application No. 10/674,971, filed on Sep. 30, 2003, now Pat. No. 8,673,004, which is a division of application No. 09/792,679, filed on Feb. 22, 2001, now Pat. No. 8,882,835, which is a continuation of application No. 09/263,266, filed on Mar. 5, 1999, now Pat. No. 6,241,770.

(51) Int. Cl.
A61F 2/44 (2006.01)
A61F 2/46 (2006.01)
(Continued)

(52) U.S. Cl.
CPC ............ *A61F 2/446* (2013.01); *A61F 2/4611* (2013.01); *A61F 2/30744* (2013.01); *A61F 2/442* (2013.01); *A61F 2002/2817* (2013.01); *A61F 2002/2835* (2013.01); *A61F 2002/3038* (2013.01); *A61F 2002/3055* (2013.01); *A61F 2002/3082* (2013.01); *A61F 2002/3085* (2013.01); *A61F 2002/30112* (2013.01);
(Continued)

(58) Field of Classification Search
CPC .............. A61F 2/446; A61F 2002/448; A61F 2002/4485
USPC ........................................ 623/17.11
See application file for complete search history.

(56) References Cited

U.S. PATENT DOCUMENTS 2,677,369 A 5/1954 Knowles
3,426,364 A 2/1969 Lumb
(Continued)

FOREIGN PATENT DOCUMENTS

DE 35 05 567 6/1986
EP 0 077 159 4/1983
(Continued)

OTHER PUBLICATIONS

Zindrick et al.; Lumbar Spine Fusion: Different Types and Indications; The Lumbar Spine, vol. 1, Second Edition, pp. 588-593 (1996).
(Continued)

*Primary Examiner* — David H Willse
(74) *Attorney, Agent, or Firm* — Martin & Ferraro, LLP

(57) ABSTRACT

An interbody spinal fusion implant adapted for placement at least in part across an intervertebral space formed across a disc space between two adjacent vertebral bodies and for penetrating engagement into each of those vertebral bodies, the implant having a trailing end adapted to sit upon and not protrude from the anterolateral peripheral rim of bone of the vertebral body.

26 Claims, 10 Drawing Sheets

(51) Int. Cl.
 *A61F 2/30* (2006.01)
 *A61F 2/28* (2006.01)
(52) U.S. Cl.
 CPC .......... *A61F 2002/30138* (2013.01); *A61F 2002/30143* (2013.01); *A61F 2002/30153* (2013.01); *A61F 2002/30235* (2013.01); *A61F 2002/30327* (2013.01); *A61F 2002/30331* (2013.01); *A61F 2002/30382* (2013.01); *A61F 2002/30599* (2013.01); *A61F 2002/30774* (2013.01); *A61F 2002/30785* (2013.01); *A61F 2002/30787* (2013.01); *A61F 2002/30797* (2013.01); *A61F 2002/30808* (2013.01); *A61F 2002/30858* (2013.01); *A61F 2002/448* (2013.01); *A61F 2002/4475* (2013.01); *A61F 2220/0033* (2013.01); *A61F 2230/0004* (2013.01); *A61F 2230/0017* (2013.01); *A61F 2230/0019* (2013.01); *A61F 2230/0069* (2013.01); *A61F 2250/0039* (2013.01); *A61F 2250/0063* (2013.01)

(56) References Cited

U.S. PATENT DOCUMENTS

| | | |
|---|---|---|
| 3,848,601 A | 11/1974 | Ma et al. |
| 3,867,728 A | 2/1975 | Stubstad et al. |
| 3,875,595 A | 4/1975 | Froning |
| 3,905,047 A | 9/1975 | Long |
| D245,259 S | 8/1977 | Shen |
| 4,070,514 A | 1/1978 | Eatherly |
| 4,309,777 A | 1/1982 | Patil |
| 4,349,921 A | 9/1982 | Kuntz |
| 4,501,269 A | 2/1985 | Bagby |
| RE31,865 E | 4/1985 | Roux |
| 4,599,086 A | 7/1986 | Doty |
| 4,636,217 A | 1/1987 | Ogilvie et al. |
| 4,714,469 A | 12/1987 | Kenna |
| 4,743,256 A | 5/1988 | Brantigan |
| 4,759,766 A | 7/1988 | Buettner-Janz et al. |
| 4,759,769 A | 7/1988 | Hedman et al. |
| 4,820,305 A | 4/1989 | Harms et al. |
| 4,834,757 A | 5/1989 | Brantigan |
| 4,863,476 A | 9/1989 | Shepperd |
| 4,863,477 A | 9/1989 | Monson |
| 4,877,020 A | 10/1989 | Vich |
| 4,878,915 A | 11/1989 | Brantigan |
| 4,904,261 A | 2/1990 | Dove et al. |
| 4,911,718 A | 3/1990 | Lee et al. |
| 4,936,848 A | 6/1990 | Bagby |
| 4,955,908 A | 9/1990 | Frey et al. |
| 4,961,740 A | 10/1990 | Ray et al. |
| 5,015,247 A | 5/1991 | Michelson |
| 5,015,255 A | 5/1991 | Kuslich |
| 5,026,373 A | 6/1991 | Ray et al. |
| 5,047,055 A | 9/1991 | Bao |
| 5,055,104 A | 10/1991 | Ray |
| 5,059,193 A | 10/1991 | Kuslich |
| 5,062,845 A | 11/1991 | Kuslich et al. |
| 5,071,437 A | 12/1991 | Steffee |
| 5,122,130 A | 6/1992 | Keller |
| 5,123,926 A | 6/1992 | Pisharodi |
| 5,171,278 A | 12/1992 | Pisharodi |
| 5,192,327 A | 3/1993 | Brantigan |
| 5,246,458 A | 9/1993 | Graham |
| 5,258,031 A | 11/1993 | Salib et al. |
| 5,290,312 A | 3/1994 | Kojimoto et al. |
| 5,306,308 A | 4/1994 | Gross et al. |
| 5,306,309 A | 4/1994 | Wagner et al. |
| 5,370,697 A | 12/1994 | Baumgartner |
| 5,397,364 A | 3/1995 | Kozak et al. |
| 5,423,855 A | 6/1995 | Marienne |
| 5,425,772 A | 6/1995 | Brantigan |
| 5,443,514 A | 8/1995 | Steffee |
| 5,458,638 A | 10/1995 | Kuslich et al. |
| 5,484,437 A | 1/1996 | Michelson |
| 5,489,307 A | 2/1996 | Kuslich et al. |
| 5,489,308 A | 2/1996 | Kuslich et al. |
| 5,507,813 A | 4/1996 | Dowd et al. |
| 5,522,899 A | 6/1996 | Michelson |
| 5,534,031 A * | 7/1996 | Matsuzaki et al. ......... 623/17.11 |
| 5,571,109 A | 11/1996 | Bertagnoli |
| D377,527 S | 1/1997 | Michelson |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,645,084 A | 7/1997 | McKay |
| 5,645,598 A | 7/1997 | Brosnahan, III |
| 5,658,337 A | 8/1997 | Kohrs et al. |
| 5,669,909 A | 9/1997 | Zdeblick et al. |
| 5,683,463 A | 11/1997 | Godefroy et al. |
| 5,702,449 A | 12/1997 | McKay |
| 5,741,253 A | 4/1998 | Michelson |
| 5,766,252 A | 6/1998 | Henry et al. |
| 5,772,661 A | 6/1998 | Michelson |
| 5,776,199 A | 7/1998 | Michelson |
| 5,782,919 A | 7/1998 | Zdeblick et al. |
| D397,439 S | 8/1998 | Koros et al. |
| 5,800,547 A | 9/1998 | Schafer et al. |
| 5,800,550 A | 9/1998 | Sertich |
| 5,814,084 A | 9/1998 | Grivas et al. |
| 5,846,484 A | 12/1998 | Scarborough et al. |
| 5,860,973 A | 1/1999 | Michelson |
| 5,861,041 A | 1/1999 | Tienboon |
| 5,865,845 A | 2/1999 | Thalgott |
| 5,888,222 A | 3/1999 | Coates et al. |
| 5,888,226 A | 3/1999 | Rogozinski |
| 5,888,227 A | 3/1999 | Cottle |
| 5,899,939 A | 5/1999 | Boyce et al. |
| 5,904,719 A | 5/1999 | Errico et al. |
| 5,906,635 A | 5/1999 | Maniglia |
| 5,972,368 A | 10/1999 | McKay |
| 5,989,289 A | 11/1999 | Coates et al. |
| 6,033,438 A | 3/2000 | Bianchi et al. |
| 6,034,295 A | 3/2000 | Rehberg et al. |
| 6,037,519 A | 3/2000 | McKay |
| 6,039,762 A | 3/2000 | McKay |
| D425,989 S | 5/2000 | Michelson |
| 6,080,155 A | 6/2000 | Michelson |
| 6,083,228 A | 7/2000 | Michelson |
| 6,111,164 A | 8/2000 | Rainey et al. |
| 6,113,638 A | 9/2000 | Williams et al. |
| 6,120,503 A | 9/2000 | Michelson |
| 6,136,031 A | 10/2000 | Middleton |
| 6,139,550 A | 10/2000 | Michelson |
| 6,143,032 A | 11/2000 | Schafer et al. |
| 6,159,214 A | 12/2000 | Michelson |
| 6,165,219 A * | 12/2000 | Kohrs et al. ............... 623/17.11 |
| 6,174,311 B1 | 1/2001 | Branch et al. |
| 6,179,875 B1 | 1/2001 | Von Strempel |
| 6,200,347 B1 | 3/2001 | Anderson et al. |
| 6,206,922 B1 | 3/2001 | Zdeblick et al. |
| 6,206,923 B1 | 3/2001 | Boyd et al. |
| 6,210,412 B1 | 4/2001 | Michelson |
| 6,224,631 B1 | 5/2001 | Kohrs |
| 6,235,034 B1 | 5/2001 | Bray |
| 6,241,770 B1 | 6/2001 | Michelson |
| 6,241,771 B1 | 6/2001 | Gresser |
| 6,245,108 B1 | 6/2001 | Biscup |
| 6,258,125 B1 | 7/2001 | Paul et al. |
| 6,277,149 B1 | 8/2001 | Boyle et al. |
| 6,294,041 B1 | 9/2001 | Boyce et al. |
| 6,294,187 B1 | 9/2001 | Boyce et al. |
| 6,348,071 B1 | 2/2002 | Steffee et al. |
| 6,350,283 B1 | 2/2002 | Michelson |
| 6,371,988 B1 | 4/2002 | Pafford et al. |
| 6,383,221 B1 | 5/2002 | Scarborough et al. |
| 6,395,031 B1 | 5/2002 | Foley et al. |
| 6,398,811 B1 | 6/2002 | McKay |
| 6,423,095 B1 | 7/2002 | Van Hoeck et al. |
| 6,482,233 B1 | 11/2002 | Aebi et al. |
| 6,482,584 B1 | 11/2002 | Mills et al. |

(56) References Cited

U.S. PATENT DOCUMENTS

| | | |
|---|---|---|
| 6,485,517 B1 | 11/2002 | Michelson |
| 6,511,509 B1 | 1/2003 | Ford et al. |
| 6,562,072 B1 | 5/2003 | Fuss et al. |
| 6,575,981 B1 | 6/2003 | Boyd et al. |
| 6,610,065 B1 | 8/2003 | Branch et al. |
| 6,666,890 B2 | 12/2003 | Michelson |
| 6,749,636 B2 | 6/2004 | Michelson |
| 6,855,168 B2 | 2/2005 | Crozet |
| 6,890,355 B2 | 5/2005 | Michelson |
| 6,989,031 B2 | 1/2006 | Michelson |
| 7,022,137 B2 | 4/2006 | Michelson |
| 7,048,762 B1 | 5/2006 | Sander et al. |
| 7,087,082 B2 | 8/2006 | Paul et al. |
| 7,156,875 B2 | 1/2007 | Michelson |
| 7,387,643 B2 | 6/2008 | Michelson |
| 7,435,262 B2 | 10/2008 | Michelson |
| 7,455,692 B2 | 11/2008 | Michelson |
| 7,462,195 B1 | 12/2008 | Michelson |
| 7,479,160 B2 | 1/2009 | Branch et al. |
| 7,534,254 B1 | 5/2009 | Michelson |
| 7,534,265 B1 | 5/2009 | Boyd et al. |
| 7,540,882 B2 | 6/2009 | Michelson |
| 7,611,536 B2 | 11/2009 | Michelson |
| 7,637,951 B2 | 12/2009 | Michelson |
| 7,637,954 B2 | 12/2009 | Michelson |
| 2001/0010020 A1 | 7/2001 | Michelson |
| 2002/0116065 A1 | 8/2002 | Jackson |
| 2002/0193881 A1 | 12/2002 | Shapiro et al. |
| 2004/0064185 A1 | 4/2004 | Michelson |
| 2004/0210313 A1 | 10/2004 | Michelson |
| 2006/0235519 A1 | 10/2006 | Michelson |
| 2009/0105821 A1 | 4/2009 | Michelson |
| 2009/0270991 A1 | 10/2009 | Michelson |
| 2010/0030333 A1 | 2/2010 | Michelson |
| 2010/0145463 A1 | 6/2010 | Michelson |
| 2011/0208313 A1 | 8/2011 | Michelson |
| 2011/0264219 A1 | 10/2011 | Rouben |
| 2013/0096687 A1 | 4/2013 | Michelson |

FOREIGN PATENT DOCUMENTS

| | | |
|---|---|---|
| EP | 0 179 695 | 4/1986 |
| EP | 0 260 044 A1 | 3/1988 |
| EP | 0 307 241 A2 | 3/1989 |
| EP | 0 392 076 A1 | 10/1990 |
| EP | 0 577 179 A1 | 1/1994 |
| EP | 0 599 419 A2 | 6/1994 |
| EP | 0 627 204 | 12/1994 |
| EP | 0 637 440 | 10/1997 |
| EP | 0 834 295 | 4/1998 |
| ES | 283078 | 5/1985 |
| FR | 2 724 312 A1 | 3/1993 |
| FR | 2 703 580 | 10/1994 |
| FR | 2 727 003 | 5/1996 |
| FR | 2 761 879 | 10/1998 |
| JP | 57-29348 | 2/1982 |
| JP | 61-122859 | 6/1986 |
| JP | 62-155846 | 7/1987 |
| JP | 5-269160 A | 10/1993 |
| WO | 92/14423 | 9/1992 |
| WO | 93/01771 | 2/1993 |
| WO | WO 95/08306 | 3/1995 |
| WO | 95/08964 | 4/1995 |
| WO | 96/22747 | 8/1996 |
| WO | WO 96/39988 | 12/1996 |
| WO | WO 96/40020 A1 | 12/1996 |
| WO | WO 97/23174 | 7/1997 |
| WO | WO 97/23175 A1 * | 7/1997 ............... A61F 2/44 |
| WO | WO 98/44877 A1 | 10/1998 |
| WO | WO 98/48738 A1 | 11/1998 |
| WO | WO 98/55052 A1 | 12/1998 |

OTHER PUBLICATIONS

Crock, H.V.; Practice of Spinal Surgery; Springer-Verlag/Wein, New York (1983), pp. 75-85.

DeBowes, R.M. et al.; Study of Bovine . . . Steel Baskets; Transactions of the 29$^{th}$ Annual Meeting; Orthopedic Research Society, vol. 8, p. 407, (Mar. 8-10, 1983).

Otero-Vich, Jose M.; Anterior Cervical Interbody Fusion with Threaded Cylindrical Bone; J. Neurosurg, vol. 63, pp. 750-753 (Nov. 1985).

Butts, M.K. et al.; Biomechanical Analysis of a New Method for Spinal Interbody Fixation; 1987 Symposium, American Society of Mechanical Engineers, "Advances in Bioengineering", Boston, MA (Dec. 13-18, 1987), 2 pages.

Crawley et al.; A Modified Cloward's Technique for Arthrodesis of the Normal Metacarpophalangeal Joint in the Horse; Veterinary Surgery, vol. 17, No. 3, pp. 117-127 (1988).

Bagby, G.W.; Arthrodesis by the Distraction-Compression Method Using a Stainless Steel Implant; Orthopedics, vol. II, No. 6., pp. 931-934 (Jun. 1987).

Itoman, M. et al.; Banked Bone Grafting for Bone Defect Repair-Clinical Evaluation of Bone Union and Graft Incorporation; J. Jpn. Orthop. Assoc., vol. 62, pp. 461-469 (1988).

Schmitz et al.; Performance of Alloplastic Materials and Design of an Artificial Disc; The Artificial Disc, Brock, Mayer, Weigel; pp. 23-24 (1991).

Fusion of the Lumbar Spine; Anterior Monosegmental Fusion L5-S1, Atlas of Spinal Operations; Thieme, pp. 270-274 (1993).

Lumbar Spine Surgery, Techniques and Complications; History of Lumbar Spine Surgery, pp. 11-15, 27, 30, 35-45, 265-268, (1994).

European Opposition Document, Nov. 27, 1995—Opposing EP Patent No. 425 542 B1 Anterior Spinal Fusion Implant.

Glaser, P.A. et al.; Biomechanical Analysis of Multilevel Fixation Methods in the Lumbar Spine; Spine, vol. 22, No. 2, pp. 171-182 (1997).

Ray, C.D.; Spinal Interbody Fusions: A Review Featuring New Generation Techniques; Neurosurgery Quarterly, 7(2), pp. 135-156 (1997).

Muschler, et al.; The Biology of Spinal Fusion; Spinal Fusion Science and Technique, Cotler and Cotler, pp. 9-13 (Dec. 1989).

U.S. Appl. No. 60/115,388, filed Jan. 11, 1999; 80 pages.

Laparoscopic Bone Dowel Surgical Technique; Brochure of Sofamor Danek; 1995; 17 pages.

Laparoscopic Bone Dowel Instruments; Brochure of Sofamor Danek; 1995; 2 pages.

Brochure of University of Florida Tissue Bank; MD-I and MD-II Custom Machine Cortical Dowels; *Circa* 1996; 2 pages.

Brochure of University of Florida Tissue Bank; MD-III Threaded Cortical Dowel; *Circa* 1996; 4 pages.

A picture of a Medtronic, Sofamor Danek Display; titled "Evolving With Your Needs;" Apr. 6, 2000; 1 page.

International Search Report mailed Aug. 14, 2000 from corresponding International PCT Application No. PCT/US00/12363, filed May 5, 2000; 3 pages.

International Search Report mailed on Aug. 15, 2001, of corresponding International Application No. PCT/US01/11723, filed Apr. 19, 2001; 2 pages.

U.S. Appl. No. 60/118,793, filed Feb. 4, 1999; 41 pages.

* cited by examiner

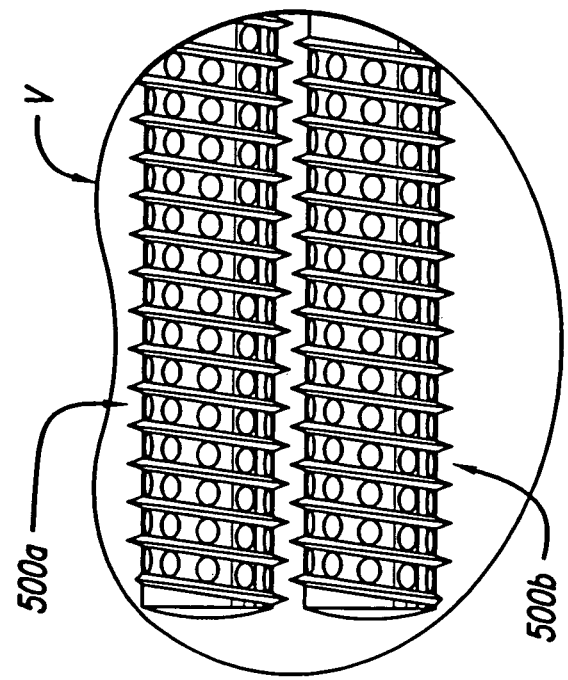
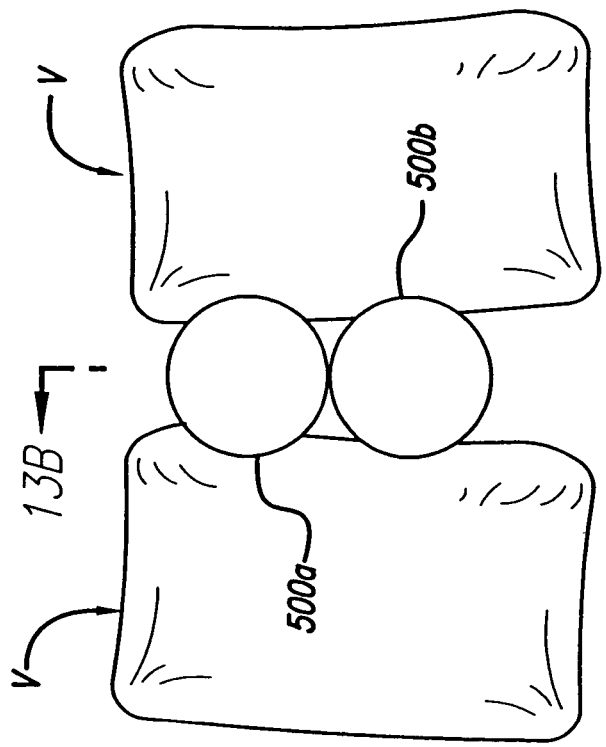

ARCUATE INTERBODY SPINAL FUSION IMPLANT HAVING A REDUCED WIDTH AND AN ANATOMICALLY CONFORMED TRAILING END

This application is a divisional of U.S. application Ser. No. 10/674,971, filed Sep. 30, 2003, now U.S. Pat. No. 8,673,004; which is a divisional of U.S. application Ser. No. 09/792,679, filed Feb. 22, 2001, now U.S. Pat. No. 8,882,835; which is a continuation of U.S. application Ser. No. 09/263,266, filed Mar. 5, 1999, now U.S. Pat. No. 6,241,770; all of which are incorporated herein by reference.

BACKGROUND OF THE INVENTION

1. Field of the Invention

The present invention relates generally to interbody spinal fusion implants that are securely placed into the intervertebral space created across the spinal disc between two adjacent vertebral bodies after the removal of damaged spinal disc material and preferably at least some vertebral bone from each of the adjacent vertebral bodies for the purpose of achieving interbody spinal fusion, which fusion occurs preferably at least in part through the spinal fusion implant itself. In particular, the present invention is directed to an improved, interbody spinal fusion implant having opposed arcuate surfaces for penetrably engaging each of the vertebral bodies adjacent a disc space in the human spine and having a trailing end configured to conform to the anatomic contour of the anterior and/or lateral aspects of the vertebral bodies, so as to not protrude beyond the curved contours thereof, and in one preferred embodiment of the present invention the above described implants are structurally adapted to be rotated for proper insertion.

2. Description of the Related Art

Surgical interbody spinal fusion generally refers to the methods for achieving a bridge of bone tissue in continuity between adjacent vertebral bodies and across the disc space to thereby substantially eliminate relative motion between the adjacent vertebral bodies. The term "disc space" refers to the space between adjacent vertebrae normally occupied by a spinal disc.

Human vertebral bodies have a hard outer shell of compact bone (sometimes referred to as the cortex) and a relatively softer, inner mass of cancellous bone. Just below the cortex adjacent the disc is a region of bone referred to herein as the "subchondral zone". The outer shell of compact bone (the boney endplate) adjacent to the spinal disc and the underlying subchondral zone are together herein referred to as the boney "end plate region" and, for the purposes of this application, is hereby so defined to avoid ambiguity. A circumferential ring of dense bone extends around the perimeter of the endplate region and is the mature boney successor of the "apophyseal growth ring". This circumferential ring comprises of very dense bone and for the purposes of this application will be referred to as the "apophyseal rim". The spinal disc that normally resides between the adjacent vertebral bodies maintains the spacing between those vertebral bodies and, in a healthy spine, allows for the normal relative motion between the vertebral bodies.

Reference is made throughout this Background section to the attached drawings in order to facilitate an understanding of the related art and problems associated therewith. In FIG. 1, a cross-sectional top plan view of a vertebral body V in the lumbar spine is shown to illustrate the dense bone of the apophyseal rim AR present at the perimeter of the vertebral body V about the endplate region and an inner mass of cancellous bone CB. The structure of the vertebral body has been compared to a core of wet balsa wood encased in a laminate of white oak. From the top plan view in FIG. 1, it can be seen that the best structural bone is peripherally disposed.

FIG. 2 is a top plan view of a fourth level lumbar vertebral body V shown in relationship anteriorly with the aorta and vena cava (collectively referred to as the "great vessels" GV).

FIG. 3 is a top plan view of a fifth lumbar level vertebral body V shown in relationship anteriorly with the iliac arteries and veins referred to by the designation "IA-V". The location of these fragile blood vessels along the anterior aspects of the lumbar vertebrae makes it imperative that no hardware protrude dangerously therefrom where the vessels could be endangered.

Implants for use in human spinal surgery can be made of a variety of materials such as surgical quality metals, ceramics, plastics and plastic composites, cortical bone and other materials suitable for the intended purpose, and further may be absorbable and or bioactive as in being osteogenic. Fusion implants preferably have a structure designed to promote fusion of the adjacent vertebrae by allowing bone to grow through the implant from vertebral body to adjacent vertebral body to thereby fuse the adjacent vertebrae. This type of implant is intended to remain indefinitely within the patient's spine or if made of bone or other resorbable material to eventually be replaced with the patient's bone.

Michelson, Ray, Bagby, Kuslich, and others have taught the use of hollow, threaded perforated cylinders to be placed across a disc space between two adjacent vertebrae in the human spine to encourage interbody spinal fusion by the growth of bone from one vertebra adjacent a disc to the other vertebra adjacent that disc through such implants. Michelson, Zdeblick and others have also taught the use of similar devices that either have truncations of their sides such that they are not complete cylinders, and/or are tapered along their longitudinal axis much like a cylinder which has been split longitudinally and then wedged apart. All of these implants have in common opposed arcuate surfaces for penetrably engaging into each of the vertebral bodies adjacent a disc space to be fused. Such implants now in common use throughout the spine, may be used individually or inserted across the disc space in side-by-side pairs, and may be insertable from a variety of directions.

It is commonly held by surgeons skilled in the art of spinal fusion that the ability to achieve spinal fusion is inter alia directly related to the vascular surface area of contact over which the fusion can occur, the quality and the quantity of the fusion mass (e.g. bone graft), and the stability of the construct. However, the overall size of interbody spinal fusion implants is limited by the shape of the implants relative to the natural anatomy of the human spine. For example, such implants cannot dangerously protrude from the spine where they might cause injury to one or more of the proximate vital structures including the large blood vessels.

With reference to FIG. 4, a top plan view of the endplate region of a vertebral body V is shown to illustrate the area H available to safely receive an implant(s) inserted from the anterior aspect (front) of the spine, with the blood vessels retracted.

As can be seen in FIG. 5, a top plan view of the endplate region of a vertebral body V with the outlines of two differentially sized prior art implants A and B installed, one on each side of the midline of the vertebral body V, are shown. The implantation of such prior art implants A and B is limited by their configuration and the vascular structures present adjacent anteriorly to the implantation space. For example, the great vessels GV present at the $L_4$ level and above are shown in solid line in FIG. 5, and for the L.sub.5 and S.sub.1 levels, the iliac artery and vein IA-V are shown in dotted line. As shown in FIG. 5, prior art implant A represents an attempt by the surgeon to optimize the length of the implant which is inhibited by a limiting corner LC. Implant A, the longest prior art implant that can be inserted without interfering with the great vessels GV adjacent the vertebral body V, leaves crosshatched area X of a cross section the vertebral body at the endplate region wasted which would be a very useful surface for contact for fusion and for support of the implant by the vertebral body. Similarly, implant B is an attempt by the surgeon to optimize the width of an implant which is also inhibited by a limiting corner LC'. Implant B, the widest prior art implant that can be inserted without interfering with the great vessels GV adjacent the vertebral body V, leaves crosshatched area Y of the cross section of the vertebral body adjacent the endplate region wasted which could otherwise be a very useful surface area for contact for fusion and for support of the implant by the vertebral body. The presence of limiting corners LC and LC' on any such implants precludes the surgeon from safely utilizing an implant having both the optimal width and length, that is the length of implant A and the width of implant B combined, as such an implant would markedly protrude from the spine and endanger the large blood vessels.

FIG. 5 illustrates the maximum dimensions for the above discussed prior art implants A and B to be safely contained within the spine so that a corner LC or LC' of the trailing end (side wall to trailing end junction) or the most rearward extension of that sidewall does not protrude outward beyond the rounded contour of the anterior (front) or the anterolateral (front to side) aspect of the vertebral bodies. Prior art implant A maximizes length, but sacrifices width and for the most part fails to sit over the best supportive bone peripherally of the apophyseal rim as previously shown in FIG. 1. Prior implant B maximizes width, but sacrifices length and again fails to sit over the best structural bone located peripherally in the apophyseal rim of the vertebral body, comprising of the cortex and dense subchondral bone. Both prior art implants A and B fail to fill the area available with a loss of both vital surface area over which fusion could occur and a loss of the area available to bear the considerable loads present across the spine.

Similarly, FIG. 6A shows the best prior art cross-sectional area fill for a pair of inserted threaded implants G as per the current prior art. Note the area Y anterior to the implants G, including the excellent structural bone of the apophyseal rim AR, is left unused, and thus implants G fail to find the best vertebral support. Since the wasted area Y anterior to the implants G is three dimensional, it also wastes a volume that optimally could be utilized to hold a greater quantity of osteogenic material. Finally, the implants of the prior art fail to achieve the optimal stability that could be obtained by utilizing the greater available surface area of contact and improved length that an implant with the maximum width and length would have, and thereby the best lever arms to resist rocking and tilting, and increased contact area to carry further surface protrusions for providing stability by engaging the vertebrae, such as with the example shown of a helical thread.

FIG. 11 shows the best fill obtained when a prior art implant C is inserted, from a lateral approach to the spine (from a position anterior to the transverse processes of the vertebrae) referred to herein as the "translateral approach" or "translaterally" across the transverse width W of vertebral body V. Some examples of implants inserted from the translateral approach are the implants disclosed in U.S. Pat. No. 5,860,973 to Michelson and preferably inserted with the method disclosed in U.S. Pat. No. 5,772,661 to Michelson. Implant C does not entirely occupy the cross-sectional area of the end plate region and leaves cross-hatched area Z of the vertebral body V unoccupied by the implant which area would be useful for contact for fusion and for support of the implant. The configuration of the trailing corner LC" of the prior art implant C prevents implant C from being sized larger and prevents the full utilization of the surface area of contact of the vertebral body cross-sectional area resulting in a suboptimal fill of the disc space with the implant, and little of the implant sitting on the apophyseal rim.

The configuration of prior art implants prevents the utilization of the apophyseal rim bone, located at the perimeter of the vertebral body to support the implants at their trailing ends. The utilization of this dense bone would be ideal.

Therefore, there is a need for an interbody spinal fusion implant having opposed arcuate portions for penetrably engaging adjacent vertebral bodies, including implants requiring rotation for proper insertion into an intervertebral space formed across the disc space between two adjacent vertebrae, that is capable of fitting within the external perimeter of the vertebral bodies between which the implant is to be inserted to maximize the surface area of contact of the implant and vertebral bone without the danger of interfering with the great vessels adjacent to the vertebrae into which the implant is to be implanted. There exists a further need for an implant that is adapted to utilize the dense cortical bone in the perimeter of the vertebral bodies in supporting such an implant installed in a disc space.

SUMMARY OF THE INVENTION

The present invention relates to preformed, manufactured interbody spinal fusion implants for placement between adjacent vertebral bodies of a human spine at least in part across the disc space between those adjacent vertebral bodies, without dangerously extending beyond the outer dimensions of the two adjacent vertebral bodies adjacent that disc space, to maximize the area of contact of the implant with the vertebral bone. For example, the present invention specifically excludes bone grafts harvested from a patient and shaped by a surgeon at the time of surgery such as those of cancellous or corticocancellous bone. The present invention can benefit implants requiring an element of rotation for proper insertion into the implantation space, and more generally, any and all interbody spinal fusion implants having opposed arcuate surfaces spaced apart to penetrably engage within the substance of the opposed adjacent vertebral bodies, as opposed to merely contacting those vertebral bodies at their exposed boney endplates.

In one embodiment of the present invention, an implant for insertion from the anterior approach of the spine and for achieving better filling of the anterior to posterior depth of the disc space between two adjacent vertebral bodies comprises opposed arcuate portions for penetrably engaging the bone of the adjacent vertebral bodies deep into the boney endplate, a leading end which is inserted first into the disc space, and an opposite trailing end. The trailing end of this embodiment of the implant of the present invention is generally configured to conform to the natural anatomical curvature of the perimeter of the anterior aspect of vertebral bodies, such that when the implant is fully inserted and properly seated within and across the disc space, the surface area of the vertebral bone in contact with the implant is maximized safely. Moreover, the implant of the present invention is able to seat upon the dense compacted bone in the perimeter of the vertebral bodies for supporting the load through the implant when installed in the intervertebral space.

More specifically, in the present invention, while the implant overall may be enlarged relative to the sizes possible with prior implants, the limiting corner of the trailing end and side wall at the trailing end has been removed. It has been the need in the past to keep this limiting corner of the implant from protruding beyond the perimeter of the disc space that has prevented these same implants from being of the optimal-size overall so as to maximize the area of contact and to seat upon and be supported by the peripheral rim of densely compacted bone.

As another example, for an implant to be inserted from the lateral aspect of the spine, the implant of the present invention has opposed arcuate surfaces for penetrably engaging each of the vertebral bodies adjacent the disc space to be fused, a leading end which is inserted first into the disc space, and an opposite trailing end. The trailing end is configured to conform to the curvature of the lateral aspect of the perimeter of the vertebral bodies adjacent the disc space and without dangerously extending beyond the outer dimensions of the two vertebral bodies, such that when the implant is inserted in the disc space, the surface area of the vertebral bone in contact with the implant is maximized without interfering with any of the vital structures adjacent to those vertebral bodies.

The spinal implants of the present invention may also have at least one opening allowing for communication between the opposed upper and lower vertebrae engaging surfaces to permit for bone growth in continuity through the implant from the adjacent vertebral bodies for fusion across the disc space of the adjacent vertebral bodies, and through the implant.

For any of the embodiments of the present invention described herein, the implants may include protrusions or surface roughenings for engaging the bone of the vertebral bodies adjacent to the implant. The material of the implant may be an artificial material such as titanium or one of its implant quality alloys, cobalt chrome, tantalum, or any other metal appropriate for surgical implantation and use as an interbody spinal fusion implant, or ceramic, or composite including various plastics, carbon fiber composites, and can include materials which are at least in part bioresorbable. The materials of the implant also can include transplants of cortical bone or other naturally occurring materials such as coral, and the implants may further comprise osteogenic materials such as bone morphogenetic proteins, or other chemical compounds, the purpose of which is to induce or otherwise encourage the formation of bone, or fusion, including genetic material coding for production of bone.

BRIEF DESCRIPTION OF THE DRAWINGS

FIG. 13A is a side elevational view of two adjacent vertebral bodies with two implants of another embodiment of the present invention implanted translaterally side-by-side across the transverse width of the vertebrae from a lateral aspect of the spine.

FIG. 13B is a top plan view of the endplate region of a vertebral body along lines 13B-13B of FIG. 13A.

DETAILED DESCRIPTION OF THE INVENTION

Figure 1:
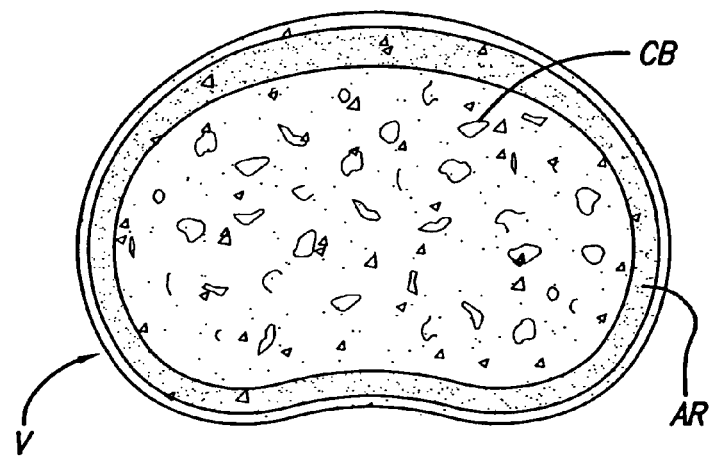
FIG. 1 is a top plan view of a horizontal cross-section through a boney endplate region of a vertebral body.
Figure 2:
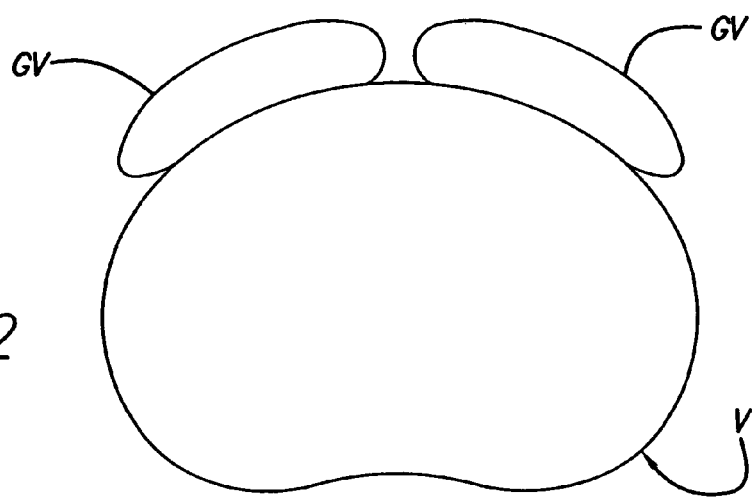
FIGS. 2-3 are top plan views of the fourth and fifth level lumbar vertebral bodies in relationship to the blood vessels located anteriorly thereto.
Figure 3:
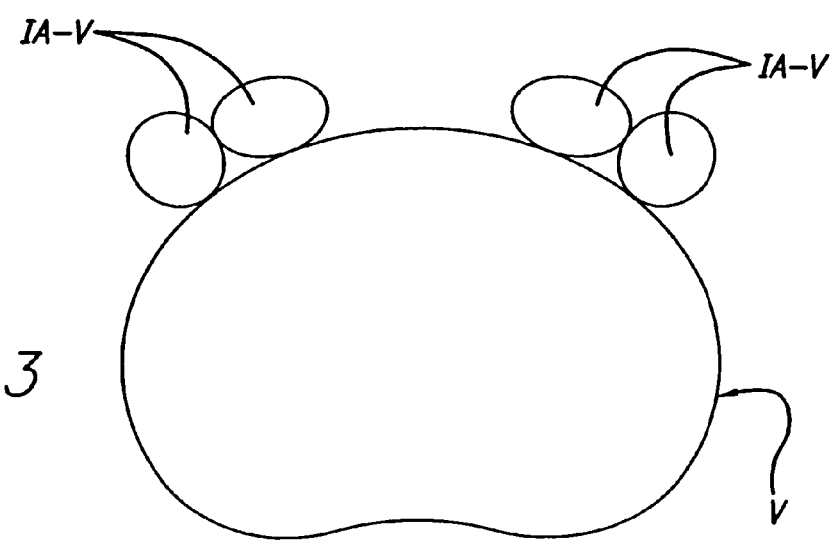
Figure 4:
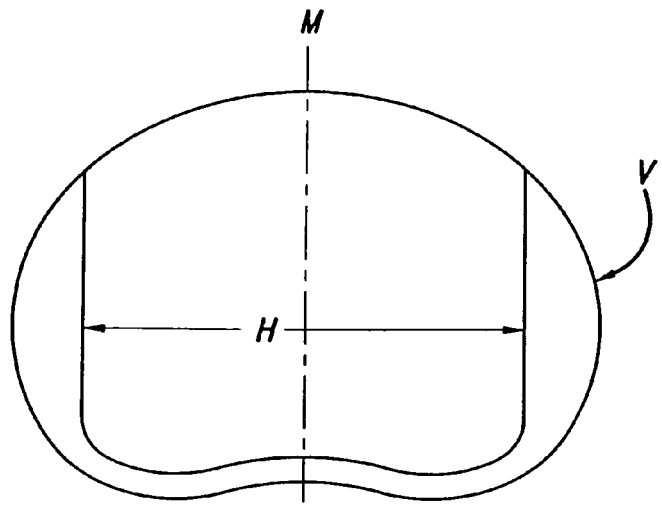
FIG. 4 is a top plan plan view of an endplate region of a vertebral body illustrating the area available to safely receive an implant(s) inserted from the anterior aspect of the spine and the area of the annulus that typically remains from an implantation from an anterior approach.
Figure 5:
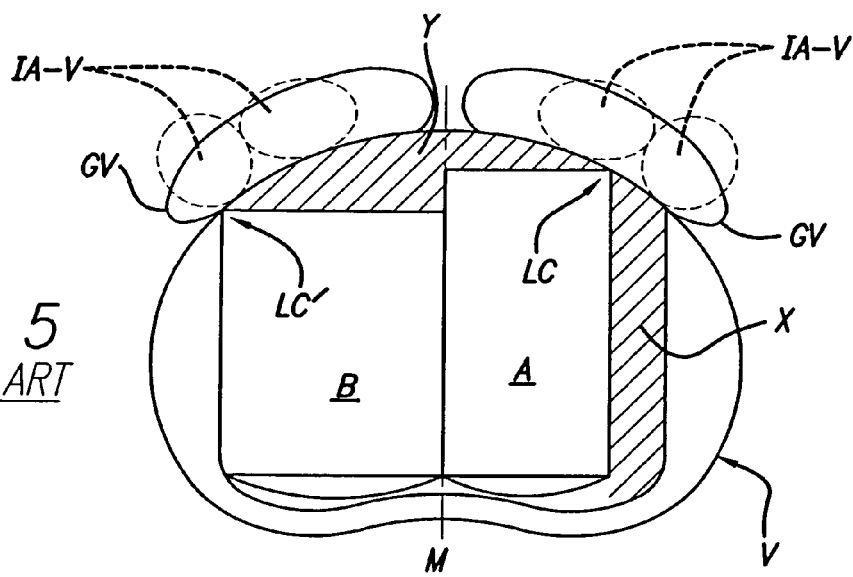
FIG. 5 is a top plan view of a lumbar vertebral body depicting the safe area of insertion for variously proportioned prior art implants for placement to either side of the midline.
Figure 6A:
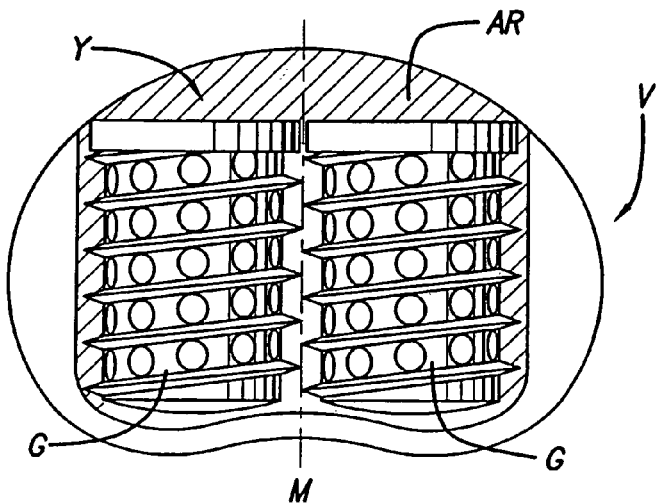
FIG. 6A is a top plan view of the endplate region of a vertebral body depicting the best fit for two threaded spinal implants of the prior art implanted on either side of the midline.
Figures 6B, 6C, 7A, 7B:
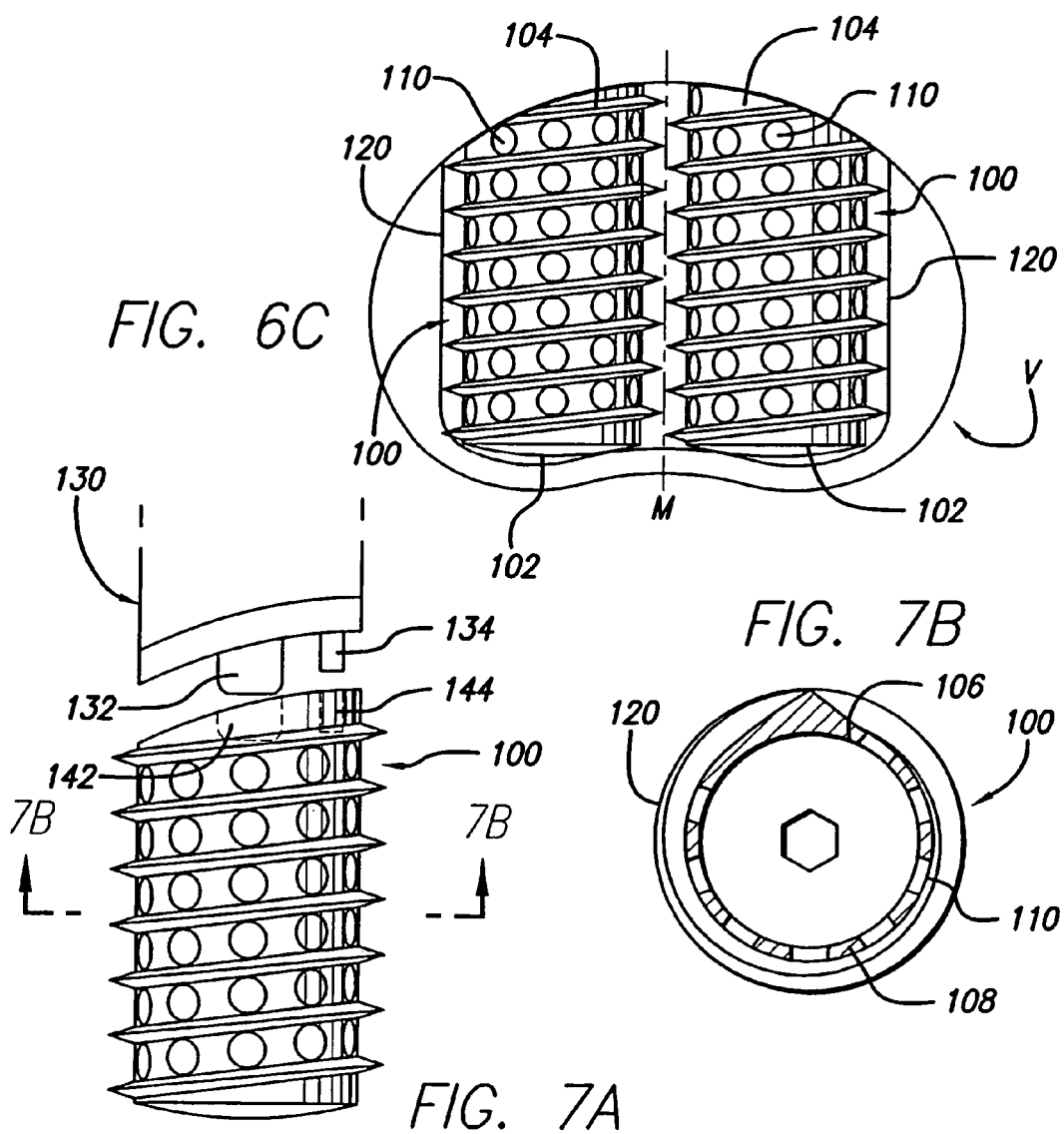
FIG. 6B is a top plan view of the endplate region of the vertebral body shown in FIG. 6A illustrating the optimal proportions and shape of an embodiment of an implant in accordance with the present invention.
FIG. 6C is a top plan view of the endplate region of the vertebral body shown in FIG. 6A and two threaded spinal fusion implants of the present invention depicting the optimal proportions and shape for such interbody fusion implants.
FIG. 7A a top plan view of threaded spinal fusion implant of the present invention with a driver instrument for engaging the trailing end of the implant.
FIG. 7B is cross-sectional view along lines 7B-7B of FIG. 7A.

FIG. 6B shows in outline form the optimal area available to be occupied by one fusion implant 100 to be inserted into the intervertebral space in side by side pairs.

With reference to FIGS. 6C, 7A, and 7B, a first embodiment of the present invention comprising an interbody spinal implant generally referred by the numeral 100, is shown inserted from the anterior aspect of a vertebral body V to each side of the midline M in the lumbar spine. In one embodiment of the present invention, implant 100 has a leading end 102 for insertion into the disc space, an opposite trailing end 104 configured to, generally conform to at least a portion of the natural anatomical curvature of the anterior aspect of the vertebral bodies adjacent the disc space, and more narrowly to be foreshortened at that aspect of the implant trailing end, that would be most lateral within the disc space when implanted within the spine. Implant 100 has opposed arcuate portions 106 and 108 that are oriented toward and adapted to penetrably engage within the adjacent vertebral bodies when inserted across the intervertebral space. Opposed arcuate portions 106 and 108 have a distance therebetween defining an implant height greater than the height of the disc space at implantation. Preferably, each of the opposed arcuate portions 106 and 108 have at least one opening 110 in communication with one another to permit for the growth of bone in continuity from the adjacent vertebral bodies and through implant 100, and as herein shown implant 100 may further be hollow or at least in part hollow. Implant 100 may also include surface roughening such as thread 100 for penetrably engaging the bone of the adjacent vertebral bodies.

As a result of its configuration, when implant 100 is inserted between two adjacent vertebral bodies, implant 100 is contained within the vertebral bodies and does not dangerously protrude from the spine. Specifically, the most lateral aspect of the implanted implant at the trailing end has been relieved, foreshortened, or contoured so as to allow the remainder of the implant to be safely enlarged so as to be larger overall than the prior art implants without the trailing end lateral wall protruding from the disc space so as to endanger the adjacent blood vessels (though overall enlargement is not a requisite element of the invention).

The present invention is not limited to use in the lumbar spine and is useful throughout the spine. In regard to use in the cervical spine, by way of example, in addition to various blood vessels the esophagus and trachea would also be at risk.

Further, the present invention includes such implants having opposed arcuate surface portions as just described whether said opposed portions are generally parallel along the length of the implant or in angular relationship to each other such that the opposed arcuate surfaces are closer to each other proximate one end of the implant than at the longitudinally opposite other end, or allowing for a variable surface, or any other configuration and relationship of the opposed arcuate surfaces.

As shown in FIG. 6C, two implants 100 are implanted into the intervertebral space side-by side. The implants 100 of the present invention optimally fill the available area and optimally sit on the anterior aphophyseal rim. It can be seen that in one embodiment of the implant 100 of the present invention, trailing end 104 is arcuate to be in conformation to the peripheral profile of the anterior aspect of the vertebral bodies where the implant is in contact with the vertebral bodies so as to allow the implant to have both a maximum safe width and length, and to sit on the peripheral vertebral body rim, including the anterior cortex and/or the apophyseal rim. This allows the implants of the present invention to have the maximum surface area of contact with the vertebrae, the greatest volume for holding osteogenic material, to sit upon the very good structural bone present at the periphery of the vertebral bodies, to have a greater surface over which to have bone engaging surface irregularities, and as a result of this combination to have the greatest stability of the implant itself and in turn to stabilize the vertebrae relative to each other.

As shown in FIG. 7A, trailing end 104 may be configured to complementary engage an instrument 130 for driving implant 100 into the installation space. Instrument 130 may have a centrally disposed projection 132 and an off-center projection 134 for engaging recesses 142 and 144 of trailing end 104, respectively. Projection 132 is preferably threaded as is recess 142.

Figure 7C:
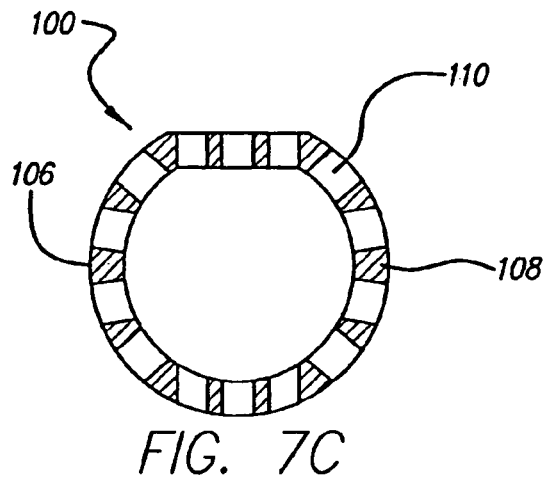
FIG. 7C is a cross sectional view of an implant having one flattened side in accordance with an embodiment of the present invention.
Figure 7D:
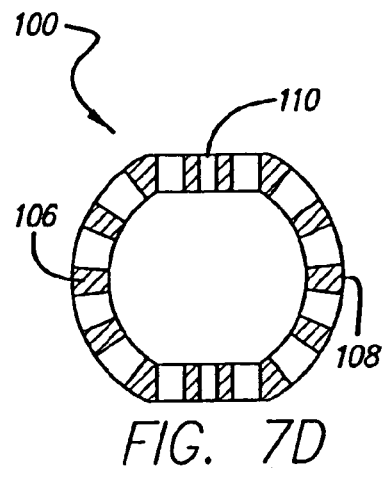
FIG. 7D is a cross sectional view of an implant having a pair of flattened sides in accordance with an embodiment of the present invention.
Figure 7E:
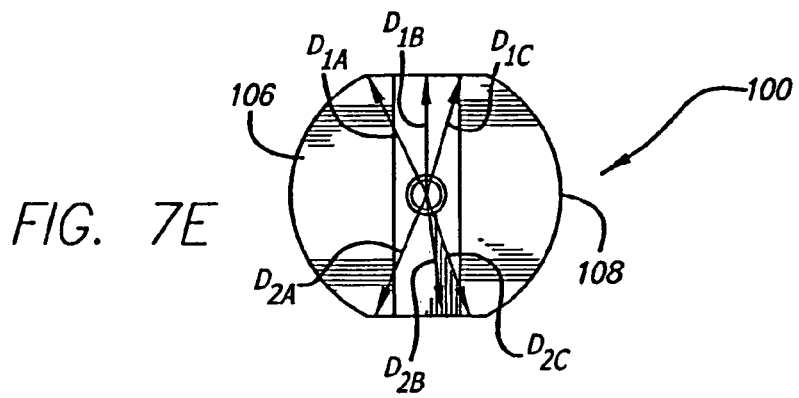
FIG. 7E is a trailing end view of an implant having a pair of flattened side in accordance with an embodiment of the present invention.
Figure 7F:
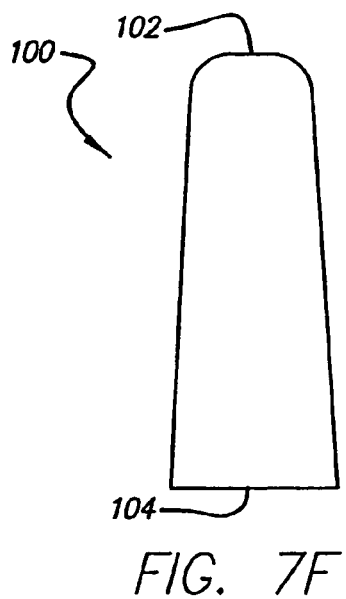
FIG. 7F is a side elevational view of an implant having opposed portions that are generally in a converging relationship to each other from a trailing end to a leading end of the implant in accordance with an embodiment of the present invention.
Figure 7G:
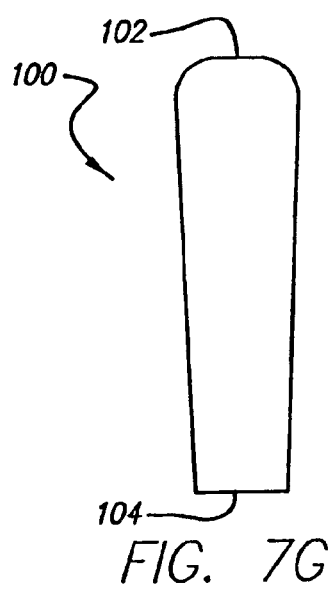
FIG. 7G is a side elevational view of an implant having opposed portions that are generally in a diverging relationship to each other from a trailing end to a leading end of the implant in accordance with an embodiment of the present invention.

While the implants of FIGS. 6C, 7A, and 7B are shown as cylindrical, the implant of the present invention includes the novel teaching as applied to any implants having opposed, at least in part, arcuate surfaces for penetrably engaging into the vertebral bodies adjacent the disc space across which the implant is implanted for the purpose of achieving fusion. These implants may have flattened or modified sides to be less wide, such as shown in FIGS. 7D and 7E. Some examples of such implants are taught by Michelson in U.S. Pat. Nos. 5,593,409 and 5,559,909, and co-pending application Ser. Nos. 08/408,908 and 08/408,928, all of which are incorporated herein by reference.

Referring to FIG. 7E, the effect of having first and second flat sides is that it is possible to have a first distance between the mid-longitudinal axis of the implant and the first flat side that is different from a second distance between the mid-longiduinal axis of the implant and the second flat side. Compare for example, distance $D_{1A}$, $D_{1B}$, and $D_{1C}$ with $D_{2A}$, $D_{2B}$, and $D_{2C}$, respectively in FIG. 7E.

Figure 8:
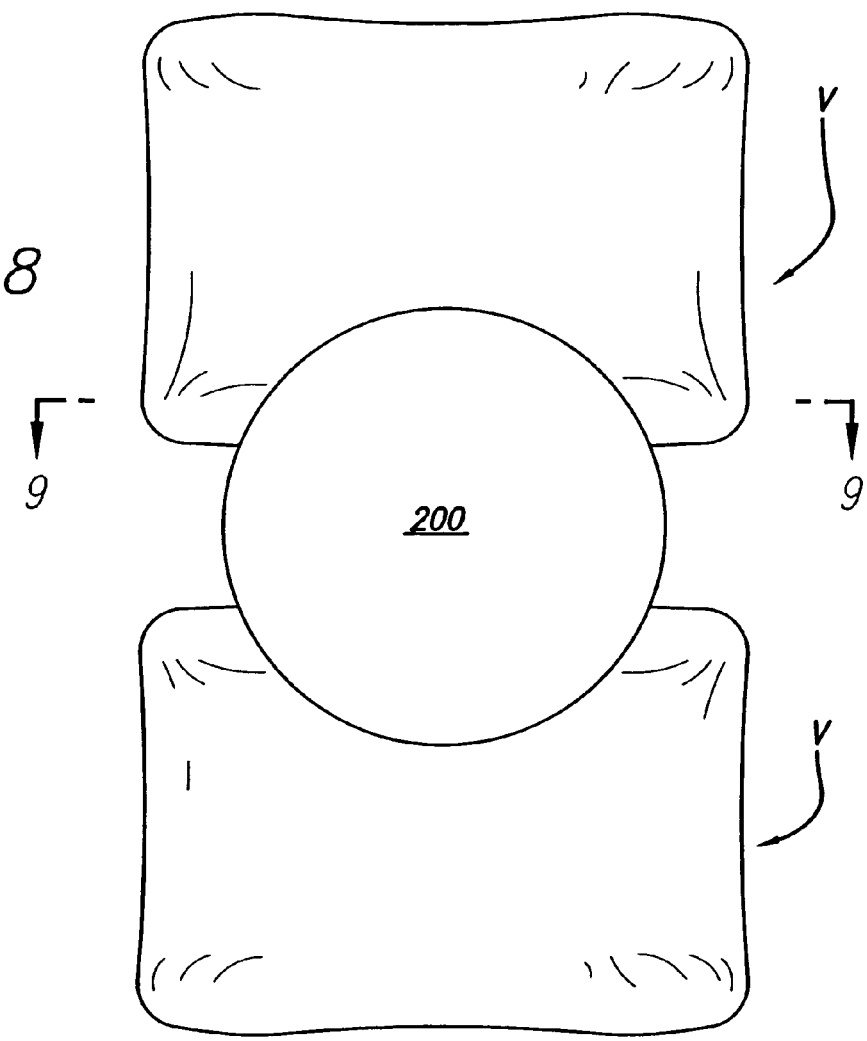
FIG. 8 is a front elevational view of two adjacent vertebral bodies with the outline of another embodiment of the implant of the present invention inserted centrally from an anterior approach to the spine.
Figure 9:
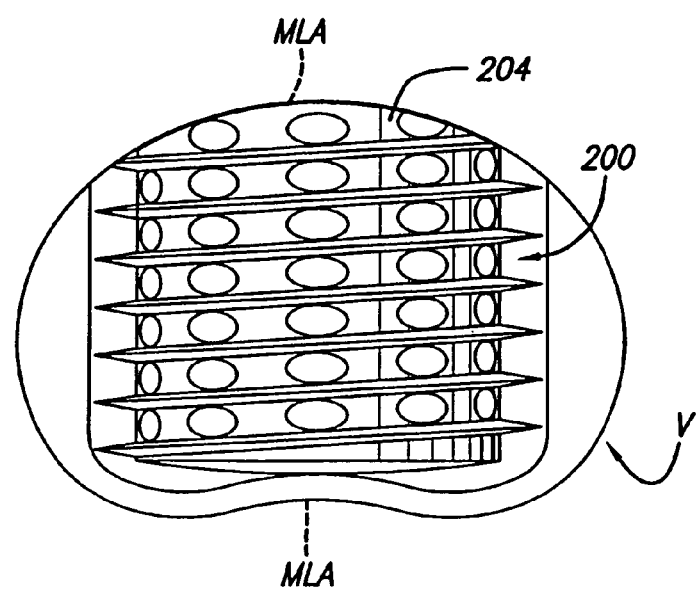
FIG. 9 is a top plan view of the endplate region of a vertebral body and implant along line 9-9 of FIG. 8.

With reference to FIGS. 8 and 9, when such a teaching is applied for use with a solitary, centrally placed implant 200 to be implanted anteriorly and generally along the midline of the disc space, the trailing end 204 of implant 200 would be arcuate as shown, such that trailing end 204 is not rotationally symmetrical about the mid-longitudinal axis MLA of implant 200, the trailing end 204 might, in a preferred embodiment, for such use be symmetrical left and right of the mid-longitudinal axis MLA when properly inserted alternatively, though not preferred, the implant 200 of FIG. 9 for implantation anteriorly could have a rotationally symmetrical, or even a rounded trailing end.

Figure 10:
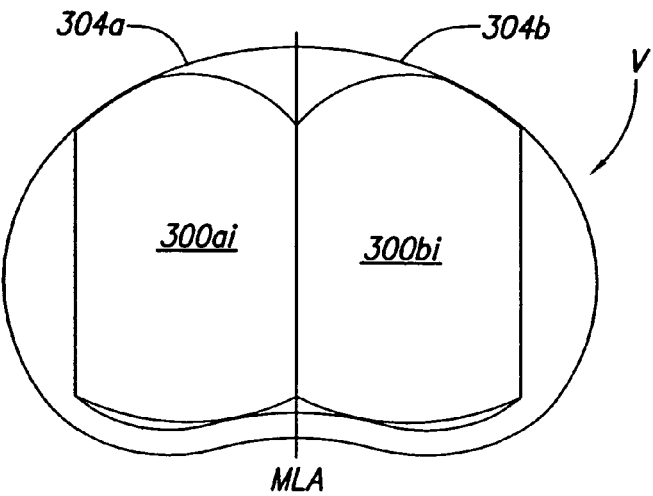
FIG. 10 is a top plan view of the endplate region of a vertebral body with the outlines of two implants in accordance with another embodiment of the present invention implanted to either side of the midline.

With reference to FIG. 10, while not achieving the maximum advantage of the present inventive teaching, implants 300a and 300b (shown in outlined form) may be used in side by side pairs, each being symmetrically arcuate left and right, but not rotationally, about the mid-longitudinal axis MLA to provide the advantage that there need not be mirror image implants or oppositely threaded (left and right) implants provided, and such implants if requiring continuing rotation for their insertion (designed to be screwed in) can be properly situated by half turns rather than full turns. That is, the correct alignment of the implant occurs every 180.degree. of rotation.

FIG. 10 further shows the area available to safely be filled and the silhouette of a pair of implants 300a and 300b having symmetrically extended trailing ends 304a and 304b for allowing for improved filling of the disc space and having relieved trailing end to side wall junctions to avoid the implant from protruding dangerously from the disc space anterolaterally. While the fill is not quite as good as with the fully asymmetric trailing end embodiment, the implants of FIG. 10 when inserted by rotation can be positioned by half-turn increments and the need for different left and right implants has been eliminated.

Figure 11:
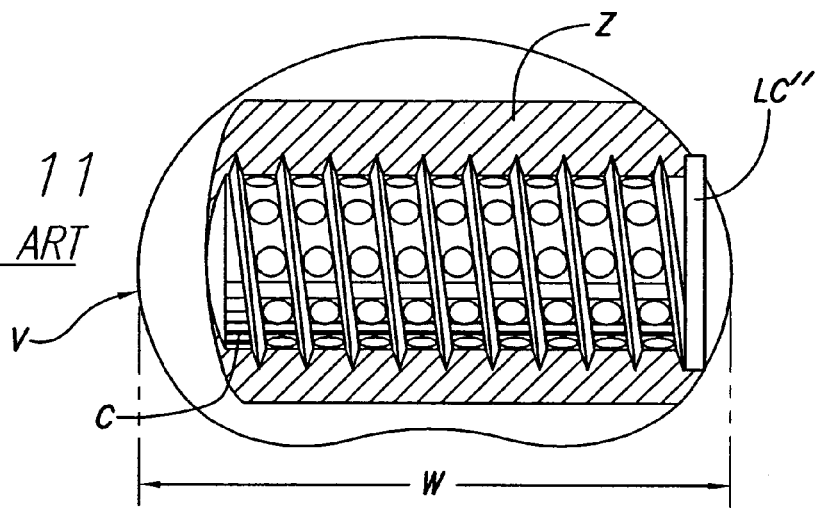
FIG. 11 is a top plan view of the endplate region of a vertebral body with a prior art implant implanted translaterally across the transverse width of the vertebral body from a lateral aspect of the spine.

As shown in FIG. 11, the best fill relative to a vertebral body achievable by prior art implant C disposed anterolaterally across the transverse width of the vertebral body is limited by corner LC" and leaves cross-hatched area Z unoccupied by implant C.

Figure 12A:
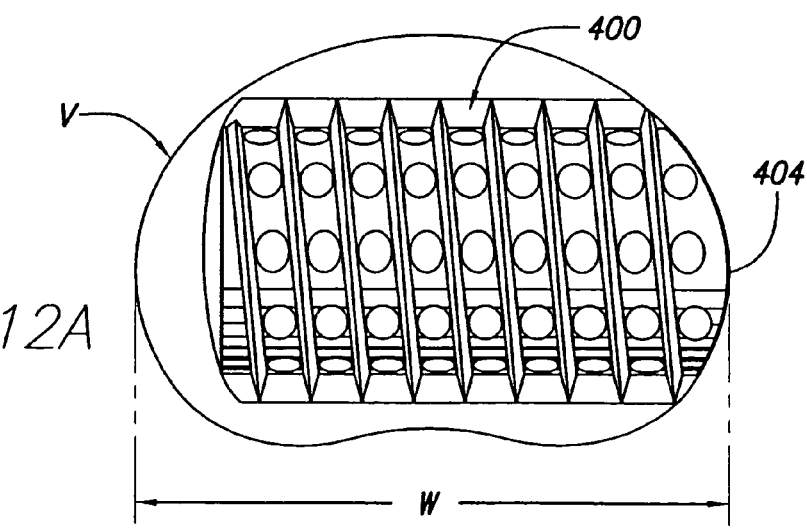
FIG. 12A is a top plan view of the endplate region of the vertebral body of FIG. 11 with an implant of the present invention implanted translaterally across the transverse width of the vertebral body from a lateral aspect of the spine.

With reference to FIG. 12A, another embodiment of the implant of the present invention referred to by the numeral 400 is shown. Implant 400 is for insertion from the anterolateral aspect of the vertebral body and FIG. 12A illustrates the greatly improved best fill made possible with implant 400. Implant 400 has a general configuration as described in U.S. Pat. No. 5,860,973 to Michelson, and has a trailing end 404 that is arcuate to generally conform to at least a portion of the natural anatomical curvature of the lateral aspect of the vertebral bodies. It is appreciated that implant 400 may include the features of implant 100 described above and trailing end 404 may be arcuate, symmetrically or asymmetrically (left and right), about the mid-longitudinal axis MLA of implant 400. In this manner, the area Z illustrated in FIG. 11 is occupied and utilized by implant 400 which can actually be not only longer overall, but also wider, or of a larger diameter, as the limiting corner LC" of the prior art implant and FIG. 11 has been removed. As evident from the drawings, the present invention moves the limiting corner LC formed by the junction of the side wall to the trailing wall or the most rearwardly protruding aspect of the laterally placed sidewall inward away from escaping the disc space.

Figure 12B:
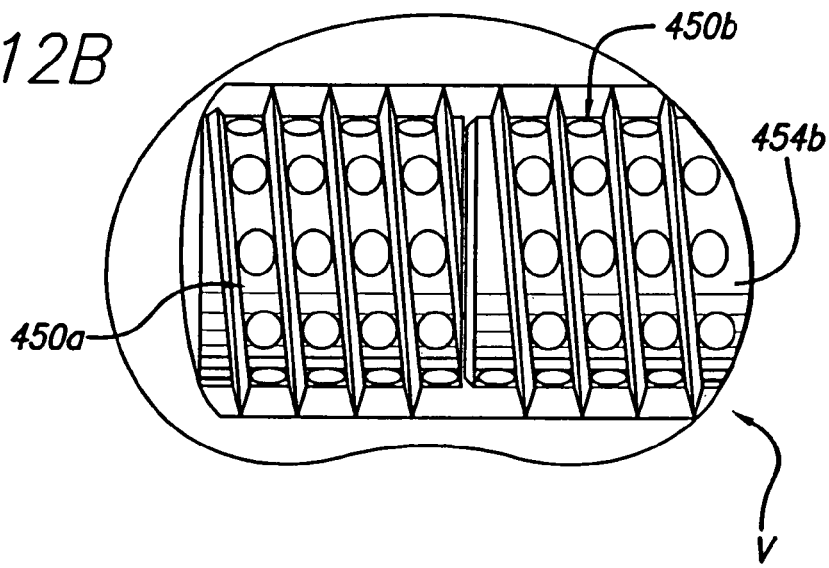
FIG. 12B is a top plan view of the endplate region of the vertebral body of FIG. 11 with an alternative embodiment of implants of the present invention implanted translaterally across the transverse width of the vertebral body from a lateral aspect of the spine, with the gap between the implants exaggerated for visual effect.

FIG. 12B is a top plan view of the endplate region of the vertebral body of FIG. 11 with an alternative embodiment of first and second implants 450a and 450b of the present invention implanted translaterally across the transverse width of the vertebral body from a lateral aspect of the spine. Implants 450a and 450b are configured such that when they are installed, they have a general configuration similar to a single implant 400 described above. Typically, implant 450a is inserted into the implantation space first, and then implant 450b is inserted into the same implantation space behind, and preferably coaxial to, implant 450a in a "box car" arrangement.

Figure 12C:
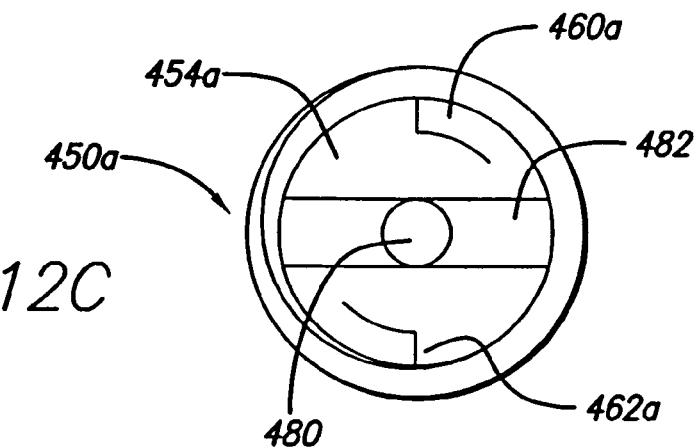
FIG. 12C is a trailing end view of a first of the implants shown in FIG. 12B.
Figure 12D:
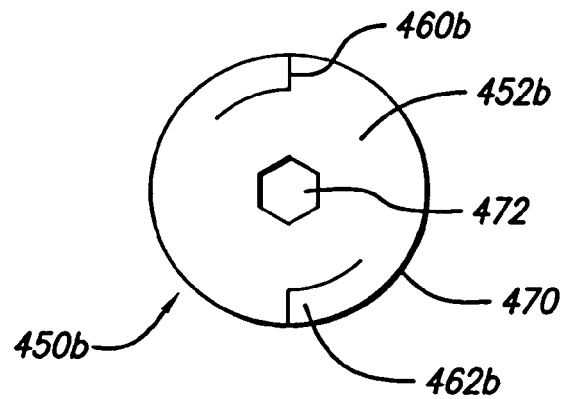
FIG. 12D is a leading end view of a second of the implants shown in FIG. 12B.

As shown in FIGS. 12C and 12D, trailing end 454a of implant 450a is configured to be placed in contact with leading end 452b of implant 450b, and preferably complementary engage leading end 452b. For example, trailing end 454a may include raised portions 460a and 462a that cooperatively engage raised portions 460b and 462b of leading end 452b of implant 450b. When implants 450a and 450b are in contact, it is possible to impart movement of implant 450a within the implantation space by movement of implant 450b. In this manner, it is possible to fine tune the depth of insertion of implant 450a without removing implant 450b. The ability to move implant 450a in this manner also prevents stripping of implant 450b due to the failure of movement of implant 450a.

Implant 450b can have a trailing end with a conventional configuration or it can have a trailing end 454b that is arcuate to generally conform to at least a portion of the natural anatomical curvature of the lateral aspect of the vertebral bodies. It is appreciated that implant 450b may include the features of implant 100 described above and trailing end 454b may be arcuate, symmetrically or asymmetrically (left and right), about the mid-longitudinal axis MLA of implant 450b. Leading end 452b may include a removable end cap 470 with a hex drive 472.

Trailing end 454a of implant 450a is preferably flat or indented concavely and may include a threaded opening 480 and a slot 482 for engaging insertion instrumentation for driving the implants. The leading end 452b of implant 450b may be flat, preferably with a bevel, chamfer, or radius, or convex to fit into the trailing end 454a of implant 450a. The radius of the leading flat edge of leading end 452b of implant 450b allows implant 450b to thread into an already tapped path created by the insertion of implant 450a and permits the external thread of implants 450a and 450b to functionally align easily.

Figure 14B:
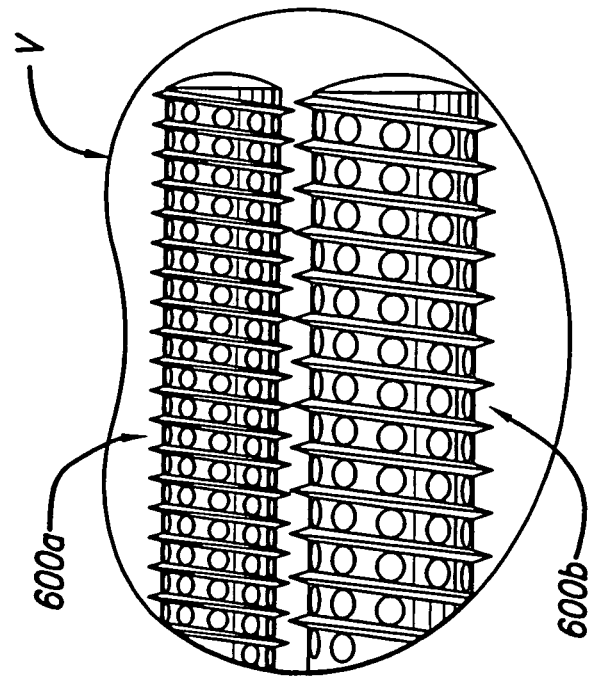
FIG. 14B is a top plan view of the endplate region of a vertebral body along line 14B-4B of FIG. 14A.
Figure 14A:
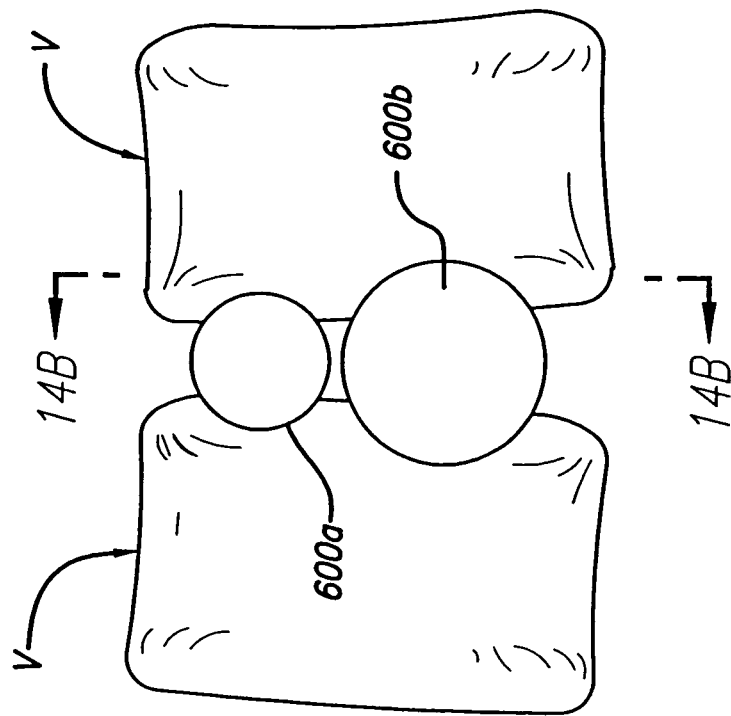
FIG. 14A is a side elevational view of two adjacent vertebral bodies with two implants of another embodiment of the present invention implanted translaterally across the transverse width of the vertebral from a lateral aspect of the spine.

FIGS. 13A and 13B demonstrate a pair of implants 500a and 500b of the present invention being used in a side-by-side relationship inserted generally laterally or anterolaterally into the spine. As shown in FIGS. 14A and 14B, two implants 600a and 600b, one anterior, one posterior, the anterior one may be of a larger diameter than the posterior one. The posterior one may be longer than the anterior one. Each may have a trailing end that is curved from side to side symmetrically or asymmetrically.

The prior art threaded implants, be they for rotation for screwing them in or for less than a full turn rotation for locking them in after they have already been linearly advanced into the spine, have all had generally straight trailing ends or trailing ends that have been rotationally symmetrical in regard to length. In contradistinction, the implants of the present invention in the preferred embodiment have trailing ends that are either arcuate or truncated to generally conform to the anterior and/or lateral (anterolateral) peripheral contours of the vertebral bodies to be fused at their trailing ends and are specifically for insertion from the anterior and anterolateral aspects of the spine and from a position anterior to the transverse processes of the vertebrae to be fused, and preferably are not rotationally symmetrical about their longitudinal axis.

While the exact curvature of a particular vertebral body may not be known, the teaching of having the implant trailing end be arcuate or truncated along one side or from side to side so as to eliminate the size limiting corner or the side wall or lateral aspect junction to the implant trailing end is of such benefit that minor differences do not detract from its benefit. Further, the range of describable curvatures may be varied proportionately with the size of the implants as well as their intended location within the spine and direction of insertion to be most appropriate and easily determinable by those of ordinary skill in the art.

Generally in the lumbar spine, the arc of radius of the curvature should be from 15 to 30 millimeters to be of greatest benefit, though it could be greater or less, and still be beneficial. The same is true for the cervical spine where the arc of radius is 10-30 mm, with 15-20 mm being preferred. Similarly, the trailing end could be curved at least in part, but not be an arc of a circle and still practice the present invention.

Figure 15A:
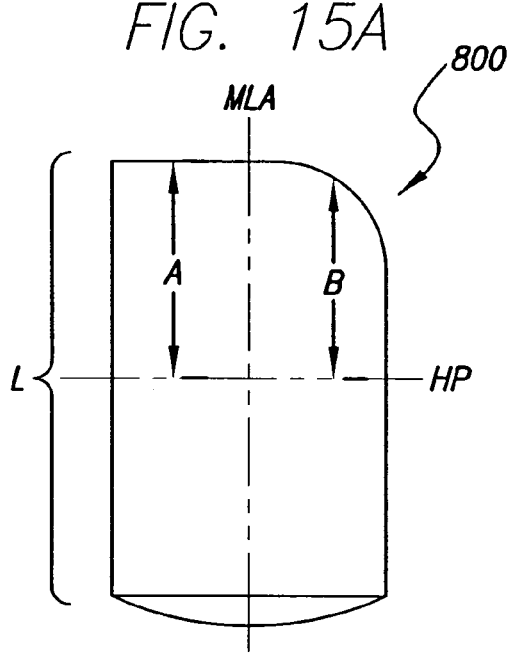
FIGS. 15A and 15B are top plan views of alternative embodiments of the implant of the present invention illustrated in outline form.
Figure 15B:
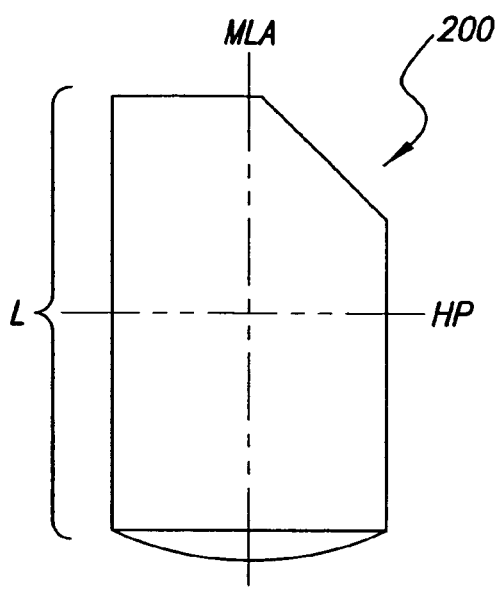

With reference to FIGS. 15A and 15B, as a substitute for contouring the entire trailing end, the trailing end may have a configuration that may be straight across and then chamfered as illustrated by implant 200 or radiused to one side only as illustrated by implant 800, sufficient to eliminate what would otherwise be a protruding corner when said implant would be properly inserted and as previously described both lateral wall rear end junctions could be chamfered or radiused.

The implants of the present invention can be configured to have a maximum distance from a horizontal plane HP perpendicular to and bisecting a length along the mid-longitudinal axis MLA of the implant and the trailing end of the implant that is greater than the distance from the horizontal perpendicular plane HP to the trailing end of at least one of the opposite side walls of the implant. This maximum distance may be greater than the distance from the perpendicular plane HP to the trailing end of both of the side walls, or the distance from the perpendicular plane HP to the trailing end of the second side wall can be greater than the distance from the perpendicular plane HP to the trailing end of the first side wall. Alternatively, the distance from the perpendicular plane to the trailing end of the second side wall can be greater than the distance along the mid-longitudinal axis from the perpendicular plane HP to the trailing end and greater than the distance from the perpendicular plane HP to the trailing end of the first side wall. The implants of the present invention may also have a maximum first length L measured along a first implant side wall that is longer than a second maximum length S measured along a second implant side wall.

As should be evident from the above discussion, all of these embodiments allow for an interbody spinal fusion implant utilizing an element of rotation for the proper insertion of the implants having at least one relieved or foreshortened aspect of at least one sidewall to end junction for placement laterally so as to not protrude unsafely from the disc space.

Figure 16A:
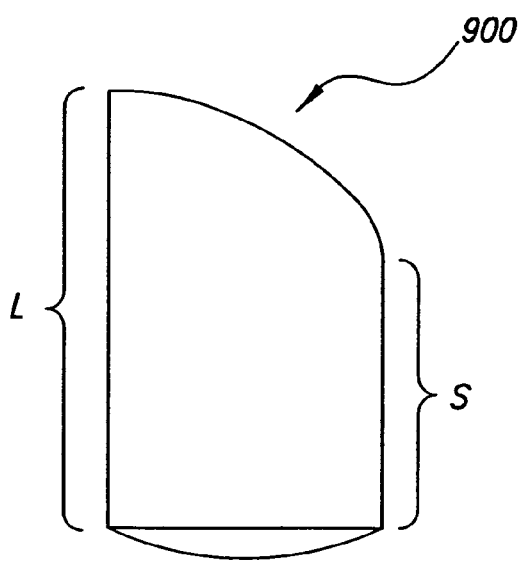
FIG. 16A is a top view of an alternative embodiment of the implant of the present invention illustrated in outline form.
Figure 16B:
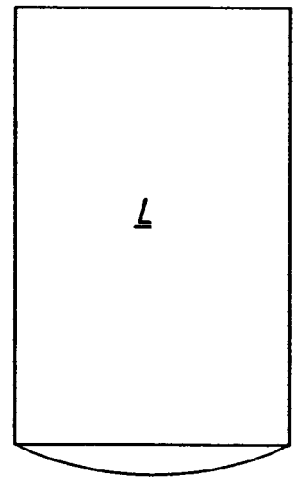
FIG. 16B is a side elevational view of the implants of FIGS. 15A, 15B, and 16A from long side "L".

As per FIGS. 16A and 16B, it should be appreciated then that a top view of the trailing end must have a convex type profile as illustrated by implant 900 while the side view will not or to a much lesser extent. That is, the trailing end of the present invention implants are rotationally asymmetrical about the mid-longitudinal axis MLA even when symmetrical from side to side, which side to side symmetrically is not a requirement of the broad inventive concept of the present invention. To have the opposed vertebrae engaging surfaces protrude dangerously beyond the perimeter of the disc space so as to impinge on the blood vessels or other vital structures proximate the spine is absolutely contrary to the teachings of the present invention which teaches a safe means for allowing the optimal sizing of the implant(s). As shown in FIG. 16B, the long sides "L" of implants 700-900 are generally the same.

While the present invention has been taught using implants requiring rotation for their insertion, this has been done to highlight that the present invention is counterintuitive and non-obvious. The additional implant length made possible by the present inventive teaching actually provides for an implant that would seem to in all but the final selected position protrude dangerously from the spine. And indeed it would except that all implants require at a minimum a clear path for their insertion. Thus, while the extended trailing portion does extend from the spine until its final rotation into correct alignment it does so when the vital structures, organs, vessels, etc., are retracted and protected and ceases to do so thereafter when those structures are released back to their normal positions in relationship to the spine.

Thus, while the present invention has been explained in regard to such implants requiring rotation for their insertion, the present invention is not so limited and is useful for all interbody spinal fusion implants having opposed arcuate upper and lower surfaces or surface portions for penetrable engagement into the bodies of vertebrae adjacent a disc space to be implanted. Moreover, such implants may include at least one opening therethrough to allow for the growth of bone from vertebral body to vertebral body and through the implant.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

While specific innovative features may have been presented in reference to specific examples, they are just examples, and it should be understood that various combinations of these innovative features beyond those specifically shown are taught such that they may now be easily alternatively combined and are hereby anticipated and claimed.

I claim:

1. A spinal fusion implant for insertion into an implantation space formed into two adjacent vertebral bodies of a human spine, said implant comprising:

a leading end for insertion into the implantation space, a trailing end opposite said leading end, a central longitudinal axis extending through said leading and trailing ends, a length between said trailing end and said leading end along the central longitudinal axis, said leading end being configured to facilitate insertion between the two adjacent vertebral bodies, and said trailing end being sized and configured to fit into the implantation space between the two adjacent vertebral bodies;

opposed upper and lower arcuate surfaces connecting said leading and trailing ends, said upper and lower arcuate surfaces including at least one opening, said openings being in communication with one another to permit for the growth of bone from adjacent vertebral body to adjacent vertebral body through said implant, said upper arcuate surface, when said implant is positioned in the implantation space, being oriented toward and facing an upper vertebral body of the two adjacent vertebral bodies, and said lower arcuate surface, when said implant is positioned in the implantation space, being oriented toward and facing a lower vertebral body of the two adjacent vertebral bodies; and a medial side having a medial side surface and a lateral side having a lateral side surface, said medial side being configured for placement adjacent a midline of the implantation space extending between anterior and posterior aspects of the human spine, said implant having first width and a second width from said medial side to said lateral side in a first plane, the first plane extending through the central longitudinal axis, through said medial and lateral sides, and through said leading and trailing ends, said implant having a maximum height from said upper arcuate surface to said lower arcuate surface in a second plane, the second plane bisecting the length of the implant along the central longitudinal axis, being perpendicular to the central longitudinal axis, and extending through said upper and lower arcuate surfaces and through said medial and lateral sides, the first width of said implant extending in the second plane and bisecting the maximum height of said implant, the second width of said implant extending in a third plane, the third plane being positioned directly adjacent said leading end, being perpendicular to the central longitudinal axis, and extending through said upper and lower arcuate surfaces, the medial side surface having a first length in the first plane from the third plane to the trailing end, the lateral side surface having a second length in the first plane from the third plane to the trailing end, the first length of said medial side surface being greater than the second length of said lateral side surface, said trailing end being at least in part arcuate in the first plane across more than half of the width of said implant and being arcuate in the first plane proximate an intersection of the first plane with a fourth plane through the central longitudinal axis, through said leading and trailing ends, and through said upper and lower arcuate surfaces, the fourth plane being perpendicular to the first, second, and third planes, said upper and lower arcuate surfaces being at least in part arcuate in the second plane adjacent the maximum height of the implant and adjacent the intersection of the second and fourth planes, and said implant having a maximum length along said medial side surface measured from the third plane to said trailing end.

2. The implant of claim 1, wherein said trailing end is adapted to conform from side to side to the peripheral contour of the vertebral bodies adjacent a disc space into which said implant is properly implanted.

3. The implant of claim 1, further comprising at least one protrusion extending from at least one of said upper and lower arcuate surfaces for engaging at least one of the adjacent vertebral bodies to maintain said implant within the implantation space.

4. The implant of claim 3, wherein said protrusion comprises a thread for engaging each of the adjacent vertebral bodies.

5. The implant of claim 4, wherein said thread extends uninterrupted along adjacent multiple turns about the central axis of said implant.

6. The implant of claim 3, wherein said protrusion comprises a ridge.

7. The implant of claim 1, further comprising a plurality of surface roughenings for engaging the adjacent vertebral bodies and for maintaining said implant in place, said surface roughenings being present on at least a portion of said upper and lower arcuate surfaces.

8. The implant of claim 1, wherein each of said upper and lower arcuate surfaces comprises an interior surface, said interior surfaces being spaced apart to define a hollow interior in communication with said openings.

9. The implant of claim 1, wherein said upper and lower arcuate surfaces have a porous surface.

10. The implant of claim 1, wherein said implant is formed of a material other than bone.

11. The implant of claim 10, wherein said implant material is selected from the group including surgical quality titanium and its alloys, cobalt chrome alloy, tantalum, any metal or alloy suitable for the intended purpose, any ceramic material suitable for the intended purpose, any plastic or composite material suitable for the intended purpose.

12. The implant of claim 1, wherein said implant is configured to require an element of rotation for proper insertion.

13. The implant of claim 1, wherein at least a portion of said implant is bioresorbable.

14. The implant of claim 1, in combination with an osteogenic material.

15. The implant of claim 14, wherein said osteogenic material includes at least one of bone, coral, bone morphogenetic protein, and genes coding for the production of bone.

16. The implant of claim 1, in combination with an instrument for inserting said implant at least in part into the disc space.

17. The implant of claim 1, wherein the maximum width and the maximum height are equal to one another.

18. The implant of claim 1, wherein said sides are at least in part parallel to one another.

19. The implant of claim 1, wherein at least one of said openings has a complete perimeter.

20. The implant of claim 1, wherein said trailing end is linear along a majority of a height thereof in the fourth plane.

21. The implant of claim 1, wherein said trailing end is continuously linear from said upper arcuate surface to said lower arcuate surface along the fourth plane.

22. The implant of claim 1, wherein said implant comprises a first spinal fusion implant, and further comprising a second spinal fusion implant insertable in the implantation space in a coaxially aligned relationship with said first spinal fusion implant.

23. The implant of claim 1, wherein a beveled portion is defined proximate said lateral side in the leading end.

24. The implant of claim 1, wherein said leading end includes an apex portion, and dimensions of said leading end in the first plane and perpendicular to the central longitudinal axis increase from said apex portion to the third plane.

25. The implant of claim 1, wherein said leading end includes an apex portion, a first dimension in the first plane directly adjacent the third plane and perpendicular to the central longitudinal axis, and a second dimension in the first plane directly adjacent said apex portion and perpendicular to the central longitudinal axis, the first dimension being greater than the second dimension.

26. The implant of claim 1, wherein a fifth plane, a sixth plane, a seventh plane, and an eight plane each extend parallel to the third plane and through the leading end, the fifth plane being directly adjacent the third plane, and dimensions of said leading end at the intersections of the fifth plane, the six plane, the seventh plane, and the eighth plane with the first plane decrease from the fifth plane to the sixth plane to the seventh plane to the eighth plane.

* * * * *

UNITED STATES PATENT AND TRADEMARK OFFICE
CERTIFICATE OF CORRECTION

| | | |
|---|---|---|
| PATENT NO. | : 9,078,768 B2 | Page 1 of 1 |
| APPLICATION NO. | : 11/133528 | |
| DATED | : July 14, 2015 | |
| INVENTOR(S) | : Gary K. Michelson | |

It is certified that error appears in the above-identified patent and that said Letters Patent is hereby corrected as shown below:

<u>In the Claims</u>:

<u>Column 12, Claim 1</u>:
Line 52: after "having" insert -- a --.

<u>Column 14, Claim 26</u>:
Line 46: change "eight" to -- eighth --; and
Line 49: change "six" to -- sixth --.

Signed and Sealed this
Tenth Day of November, 2015

Michelle K. Lee
*Director of the United States Patent and Trademark Office*